US010456290B2

(12) United States Patent
Oleson et al.

(10) Patent No.: US 10,456,290 B2
(45) Date of Patent: Oct. 29, 2019

(54) LOW-MODULUS ELASTOMERIC COMPOSITIONS AND ARTICLES MADE THEREWITH

(75) Inventors: Andrew Oleson, Bristol, PA (US); Benny Yam, Holmdel, NJ (US); Cristina Cojocariu, Bridgewater, NJ (US); Michael J. Harrison, Princeton, NJ (US); Steven Bolkan, Hopewell, NJ (US)

(73) Assignee: Church & Dwight Co., Inc., Princeton, NJ (US)

(*) Notice: Subject to any disclaimer, the term of this patent is extended or adjusted under 35 U.S.C. 154(b) by 547 days.

(21) Appl. No.: 13/979,879

(22) PCT Filed: Jan. 17, 2012

(86) PCT No.: PCT/US2012/021510
§ 371 (c)(1),
(2), (4) Date: Aug. 16, 2013

(87) PCT Pub. No.: WO2012/099853
PCT Pub. Date: Jul. 26, 2012

(65) Prior Publication Data
US 2013/0316107 A1    Nov. 28, 2013

Related U.S. Application Data

(60) Provisional application No. 61/433,827, filed on Jan. 18, 2011.

(51) Int. Cl.
| B32B 1/08 | (2006.01) |
| A61F 6/04 | (2006.01) |
| A61L 29/06 | (2006.01) |
| A61L 29/14 | (2006.01) |
| A61L 31/06 | (2006.01) |
| A61L 31/14 | (2006.01) |
| A41D 19/00 | (2006.01) |
| A61L 29/04 | (2006.01) |
| C08L 53/02 | (2006.01) |

(52) U.S. Cl.
CPC ............ *A61F 6/04* (2013.01); *A41D 19/0055* (2013.01); *A61L 29/041* (2013.01); *A61L 29/06* (2013.01); *A61L 29/141* (2013.01); *A61L 31/06* (2013.01); *A61L 31/141* (2013.01); *C08L 53/025* (2013.01); *Y10T 428/139* (2015.01); *Y10T 428/1345* (2015.01); *Y10T 428/31587* (2015.04); *Y10T 428/31837* (2015.04); *Y10T 428/31924* (2015.04); *Y10T 428/31931* (2015.04)

(58) Field of Classification Search
CPC ..... B32B 1/02; Y10T 428/13; Y10T 428/139; Y10T 428/1345; Y10T 428/31931; Y10T 428/31587; Y10T 428/31837; Y10T 428/31924; C08L 53/00; C08L 53/025; A61F 6/04; A61L 29/06; A61L 29/141; A61L 31/141; A61L 29/041; A41D 19/0056

USPC .............................. 428/34.1, 35.7, 35.9, 36.9
See application file for complete search history.

(56) References Cited

U.S. PATENT DOCUMENTS

| 4,369,284 | A | * | 1/1983 | Chen .................... A61C 15/041 44/271 |
| 4,880,878 | A | | 11/1989 | Himes et al. |
| 5,112,900 | A | | 5/1992 | Buddenhagen et al. |
| 5,191,024 | A | * | 3/1993 | Shibata ..................... C08F 8/04 525/100 |
| 5,334,646 | A | * | 8/1994 | Chen .................... A61C 15/041 132/321 |
| 5,336,708 | A | * | 8/1994 | Chen .................... A61C 15/041 132/321 |
| 5,407,715 | A | | 4/1995 | Buddenhagen et al. |
| 5,508,334 | A | * | 4/1996 | Chen .................... A61C 15/041 132/321 |
| 5,578,372 | A | * | 11/1996 | Murakami .............. B32B 27/08 156/331.7 |
| 5,633,286 | A | * | 5/1997 | Chen .................... A61C 15/041 132/321 |
| 5,806,523 | A | * | 9/1998 | Shubin, Sr. ............... A61F 6/04 128/842 |
| 5,994,450 | A | * | 11/1999 | Pearce .................. A43B 13/04 524/505 |

(Continued)

FOREIGN PATENT DOCUMENTS

| JP | 2916467 B1 * | 7/1999 |
| WO | 95/00586 A1 | 1/1995 |

(Continued)

OTHER PUBLICATIONS

Patent Examination Report No. 1, for Australian Patent Application No. 2012207516, dated Oct. 13, 2015, pp. 1-3, which corresponds to this present application.

(Continued)

*Primary Examiner* — Marc A Patterson
(74) *Attorney, Agent, or Firm* — Church & Dwight Co., Inc.

(57) ABSTRACT

The present invention provides an elastomeric composition for making elastomeric articles having at least one layer, such as but not limited to condoms, which have a deformation stress or modulus below about 1.5 MPa at 500% extension, comprising at least one polymeric material, at least one plasticizer and optionally at least one coating. The elastomeric articles also have unique tactile and tensile properties, such as conformability and low radius of curvature.

8 Claims, No Drawings

(56) References Cited

U.S. PATENT DOCUMENTS

| | | | |
|---|---|---|---|
| 6,121,366 A | 9/2000 | Sharma | |
| 6,288,159 B1 | 9/2001 | Plamthottam | |
| 6,639,007 B2 | 10/2003 | Plamthottam | |
| 7,531,594 B2* | 5/2009 | Lin | C08K 5/01 524/474 |
| 2003/0090030 A1* | 5/2003 | Ferguson | B29C 33/3857 264/220 |
| 2003/0212213 A1 | 11/2003 | Bendejacq et al. | |
| 2004/0105943 A1* | 6/2004 | Hoerner | A61L 15/24 428/35.7 |
| 2004/0127932 A1* | 7/2004 | Shah | A61F 6/04 606/193 |
| 2004/0225044 A1 | 11/2004 | Chen | |
| 2004/0231028 A1 | 11/2004 | Triebes et al. | |
| 2009/0205776 A1 | 8/2009 | Datta et al. | |

FOREIGN PATENT DOCUMENTS

| | | |
|---|---|---|
| WO | 07/58880 A2 | 5/2007 |
| WO | WO-2010/088713 A1 * | 8/2010 |

OTHER PUBLICATIONS

Extended European Search Report, pursuant to Rule 62 EPC, containing the supplementary search report and the European search opinion, for EP Application No. 12736471.9, published Jul. 5, 2016, pp. 1-7, which corresponds to the current application.

* cited by examiner

LOW-MODULUS ELASTOMERIC COMPOSITIONS AND ARTICLES MADE THEREWITH

CROSS-REFERENCE TO RELATED APPLICATIONS

This application claims priority to U.S. Provisional Application No. 61/433,827 filed on Jan. 18, 2011.

FIELD OF THE INVENTION

This invention is related to elastomeric compositions for producing low-modulus articles, such as condoms.

BACKGROUND OF THE INVENTION

Thin-walled, extensible articles such as gloves and condoms have long been made from natural rubber latex, which comprises an emulsion of natural rubber and water, stabilizers and vulcanizing agents. Typically, a form of an appropriate shape (optionally pre-coated with a coagulating solution) is dipped into the natural rubber latex mixture once or several times to build up a layer of the desired thickness. The water is then evaporated to leave behind a solid natural rubber latex film. The film is further vulcanized to provide adequate mechanical and physical properties.

Natural rubber latex offers numerous advantages for these articles, such as high durability, elasticity and good "tactility" or feeling to the user. In particular, the good tactility is believed to be a result of the low deformation stress of natural rubber latex at 10-500 percent elongations, and the high elastic recovery from these elongations.

However, natural rubber latex is not hypoallergenic due to the presence of residual surfactants, vulcanizing agents, stabilizing agents, antioxidants, or protein materials. Subsequently, individuals who are particularly susceptible to irritation or sensitization may experience allergic reactions from contacting natural rubber latex. Natural rubber latex films can also be weakened by their exposure to oil-based materials such as mineral oil, motor oil, etc.

In order to overcome the above disadvantages, various types of synthetic elastomeric polymer products have been developed instead. These articles are typically produced by dip forming from either water-based polymer, or solvent-based polymer systems that are made from the dissolution of synthetic rubber compositions in solvents.

Recently, a variety of methods and procedures have been described in the prior art for preparing thin and extensible particles with synthetic polymers. For example, U.S. Pat. No. 4,880,878 to Himes et al. describes a thermoplastic blend that absorbs less than 40% of an oil, and has a superior tensile strength. The blend comprises about 80 to about 20 phr of an elastomeric block copolymer that has a general configuration of A-B-A, wherein the B block is a butadiene hydrocarbon block that is consisted of about 35 to about 55 mole percent of condensed butadiene units in a 1,2 configuration, and about 20 to about 80 phr of a block copolymer that has a general configuration of A-B-A, wherein the B block is a hydrogenated butadiene hydrocarbon block consisting of about 18 to about 34 mole percent of condensed butadiene units in a 1,2 configuration.

Another example is U.S. Pat. Nos. 5,112,900 and 5,407,715 to Buddenhagen et al., which disclose an elastomeric liquid solution for producing gloves or condoms, comprising essentially of a block copolymer component that is comprised of at least two SEBS (styrene-block-ethylene-co-butylene-block-styrene) triblock copolymers that have different solution viscosity/copolymer concentration values; a plasticizer in an amount sufficient to provide tactility in dip formed products made from the composition; and a solvent in an amount sufficient to form a stable solution of the block copolymer component and the plasticizer. Preferably, three SEBS block copolymers form the block copolymer component, the plasticizer is mineral oil, and the plasticizer is present in an amount sufficient to reduce the deformation stress of the solid formed elastomer to less than about 5.5 MPa (millions of Pascals) at 500 percent elongation.

Another example is U.S. Pat. No. 6,639,007 to Plamthottam, which describes an elastomeric composition that includes a single SEBS block copolymer having at least about 15 weight percent of styrene end blocks, wherein the weight average molecular weight of the styrene end blocks is at least about 7,000 Daltons and the weight average molecular weight of ethylene-co-butylene midblocks is at least about 60,000 Daltons, and a plasticizer in an amount sufficient to provide tactility in products made from the composition. A form having the shape of the desired product is dipped into the composition to build up a film of the elastomeric composition on the form. The dip-formed elastomeric films are free of pinholes and resistant to oxidative and ozone attack. The films are particularly suitable for use in products such as examination surgical and industrial gloves and condoms.

However, these known synthetic rubber compositions do not have the required combination of strength, tactility and/or resistance to environmental damage required for many products such as examination and surgical gloves and condoms.

Therefore there remains a need for an improved elastomeric material for producing thin, dip-formed articles such as examination or surgical gloves and condoms. Such a material should have not only the required properties of strength and elastic elongation, but also be pinhole free when the article is formed and used, resistant to immediate environmental or damage occurring during storage or use, and be hypoallergenic. The present invention fulfills this need, and further provides related advantages.

SUMMARY OF THE INVENTION

The present invention provides an elastomeric composition for making articles of manufacture, comprising at least one plasticizer and at least one polymeric material selected from silicone, polyurethane, styrenic block copolymers (SBC) (e.g., SEBS (styrene-block-ethylene-co-butylene-block-styrene), SEPS (styrene-block-ethylene-co-propylene-block-styrene), SEEPS (styrene-block-ethylene-co-ethylene-propylene-block-styrene), SEEBS (styrene-block-ethylene-co-ethylene-butylene-block-styrene), SBS (styrene-block-butadiene-block-styrene), and SIS (styrene-block-isoprene-block-styrene)), or other elastomers. Further embodiments of the invention include at least one coating. The formulations of the invention can be applied to condoms or other devices such as gloves and catheters. The ready-made articles have a deformation stress or modulus below about 1.5 MPa at 500% extension.

DETAILED DESCRIPTION OF THE INVENTION

The present invention is directed toward an elastomeric composition for manufacturing low modulus elastomeric articles having at least one layer, such as but not limited to condoms, with deformation stress levels below about 1.5 MPa at 500% extension.

The formulation ingredients include at least one plasticizer, at least one a polymer that is dissolved in a carrier medium and optionally at least one filler. The elastomeric article has at least one layer and may contain at least one coating. The elastomeric article also has unique tactile and tensile properties, such as conformability and low radius of curvature. The terms "formulation" and "composition" are hereinafter regarded as equivalent terms.

Polymer

The polymeric material that is used in the elastomeric formulation is selected from silicone, polyurethane, styrenic block copolymers ("SBC") (e.g., SEBS (styrene-block-ethylene-co-butylene-block-styrene), SEPS (styrene-block-ethylene-co-propylene-block-styrene), SEEPS (styrene-block-ethylene-co-ethylene-propylene-block-styrene), and SEEBS (styrene-block-ethylene-co-ethylene-butylene-block-styrene), SBS (styrene-block-butadiene-block-styrene) and SIS (styrene-block-isoprene-block-styrene)), other elastomers and their mixtures thereof.

The block copolymers used in this invention may also have enhanced hydrophilicity. The enhanced hydrophilicity of block copolymers not only reduces the energy required to prepare aqueous dispersions of such block copolymers, but also yields superior mechanical properties (i.e. higher tensile strength) of the films formed from such block copolymers. The styrenic triblock copolymer SEBS is widely used as a thermoplastic elastomer. However, the non polar nature of polystyrene (PS) and poly(ethylene-co-butylene) (EB) blocks within SEBS limits its application in polar systems such as blends containing engineered plastics. Moreover, due to the non polar nature of both blocks, the energy required to disperse SEBS into water to form lattices are relatively high. Therefore, there is a need in the art to modify styrenic triblock copolymers by introducing functional groups with affinity toward water. The chemical modification of styrenic triblock copolymers can be performed by grafting methodologies such as, but not limited to: grafting carboxyl group (—COOH) on the PS blocks: the initial step is the acetylation of the PS blocks and then transforming the acetyl groups (—COCH$_3$) to —COOH via oxidation, grafting hydroxyl groups (—OH) on the PS groups: once the —COOH groups were grafted, these groups can be reduced to form —OH groups, grafting sulfo groups (—SO$_3$H) on the PS blocks: can be achieved by selective sulfonation of styrenic groups. PS blocks can also be modified though the chloromethylation process; the chlorine group thus formed can be further modified to an amine (—NH$_2$) by reaction with anhydrous ammonia. Also, grafting maleic anhydride on the EB block increases functionalization of elastomeric phase of block copolymers upon grafting functional groups thereon selected from the group consisting of: —COOH, —OH, and —NH$_2$, alone or in combination. The hydrogen bonding between these grafted polar groups increases the tensile strength of the films formed from the modified SEBS, SEPS or SEEPS block copolymers.

It is difficult to make elastomeric articles such as condoms with a wall thickness of about 70 microns via solvent solution dipping from high molecular weight linear styrenic block copolymers such as SEBS, SEPS, and SEEPS. This is due to the high viscosity of the linear styrenic block copolymers. To overcome this challenge, the present invention may utilize star styrenic block copolymers, or blends of linear styrenic block copolymers and star styrenic block copolymers. Star styrenic block copolymers have a central core and polymer chains extending from the central core, and they allow for a higher molecular weight in a given hydrodynamic volume relative to linear polymers. This means that the star styrenic block copolymers of the present invention have a similar molecular weight as the linear styrenic block copolymers but exhibit lower viscosity.

Styrenic block copolymers have phase separation due to thermodynamic incompatibility of the two phases: end-blocks styrenic phase and mid-block rubbery phase. In star styrenic block copolymers, the phase separation is also higher due to the increased organization of the molecule, and the high physical cross linking contributes to better connected pure polystyrene (PS) domains, which provide higher strength of the resultant film and articles of manufacture. The present invention includes an article of manufacture composed of a star styrenic block copolymer and blends of star styrenic block copolymers and linear styrenic block copolymers. Using star styrenic block copolymers not only leads to a reduction of solution viscosity, thus allowing easier processes for making thin condoms via a solvent dipping process, but also will increase the strength of the final product. Star block copolymers of this invention provide for increased strength and can be used in an aqueous or other solvent-based dispersion. Star block copolymers can also be added to a SBC-based system.

The elastomeric article of the present invention can be made by dipping a form into an aqueous dispersion of a block copolymer such as SEBS that is blended with natural rubber latex (NRL), synthetic polyisoprene (PI), water-based polyurethane (PU), random copolymers such as styrene-co-butadiene (SB), styrene-co-isoprene (SI), or styrenic triblock copolymers such as styrene-block-butadiene-block-styrene (SBS) and styrene-block-isoprene-block-styrene (SIS) to increase the strength of the dipped articles. After the form is dipped into the blend mixture, the form is placed in an oven at high temperature to induce chemical cross-linking (vulcanization) at the unsaturated bond of NRL, PI, SB, SIS and SBS polymers.

Accordingly, higher tensile strength of the ready-made article can be achieved by utilizing a blend of aqueous dispersions of SEBS with SEPS and/or SEEPS. Similar to SEBS, the PS blocks in SEPS and SEEPS form the physical cross-linking of elastomeric (rubbery) domains. However, the methylene group in the ethylene/propylene midblock of SEPS and SEEPS hinders the free rotation of polymer chains to increase polymer stiffness as compared to SEBS. Because the cross-linking is physical in nature, such blends do not require stabilizing or vulcanizing agents.

Alternatively, other polymeric materials that are known in the art are also suitable to be mixed with plasticizers to make elastomeric materials of the present invention.

Plasticizer

A plasticizer or a mixture of plasticizers is used in the present elastomeric formulation. Useful plasticizer is selected from mineral oil; dimethicone or its modified form with hydroxyl, carboxylic, cetyl alcohol or amine functionality; vitamin E (tocopherol); straight or slightly branched alkanes; unsaturated alkanes. Mineral oil is preferred.

The amount plasticizer used in the invention is sufficient to produce articles, such as condoms, to have a modulus of less than about 1.5 MPa at 500% extension. The amount of a plasticizer can be expressed in phr plasticizer oil (parts of plasticizer oil per hundred parts of rubber). The elastomeric formulation contains a phr plasticizer of above 100 phr, preferably about 100 to about 300 phr, more preferably about 100 to about 250 phr, and most preferably 150 to about 250 phr. However, plasticizer ranges between 100 and 200 phr are also useful in obtaining condoms having a modulus of less than about 1.5, less than 1.2 and even less than 1.0 MPa at 500% extension.

Carrier Medium

The carrier medium can be any solvent that is capable to solvate polymers such as styrene and ethylene-co-butylene. Care must be taken to ensure that the solvent is also capable to solvate any desired additives such as plasticizers and fillers. Suitable solvent carriers include toluene, ethyl acetate, methyl ethyl ketone, acetone, tetrahydrofuran, diethyl ether, dicholormethane, chloroform, dimethylformamide and mixtures thereof. A mixture of high volatile and slower drying solvents is also applicable. Such mixture allows the films to set up quickly due to the volatile solvent, prevent dripping defects, finish drying slowly, and prevent cracking of the films. A preferred solvent carrier is a 70:30 by weight mixture of tetrahydrofuran and toluene.

Alternatively, the carrier medium can also be water, or water admixed with other additives such as surfactants. Various aqueous dispersions of polymers are used in the present invention.

Filler

Filler may be included in the elastomeric formulation (i.e. SEBS-based formulations) to add strength and reduce cost. These formulations include polymeric materials such as polystyrene or polyethylene. Useful filler are selected from inorganic fillers such as calcium carbonate, talc, titanium oxide, silica, clay, carbon black, magnesium carbonate, alumina, and mixtures thereof. Particle sizes of the fillers could range from nanometers to hundreds of microns. These particles would necessarily have to be on the order of the thickness of the film, for example ca. 75 microns for a typical latex condom, or aggregate to a structure on that order. The particles could be platelets, spheres or rods.

Coating

The low modulus elastomeric articles may have at least one coating. For example, anti-bacterial coatings may be applied onto the articles to reduce the viable bacterial count of any bacteria already present on the articles' surfaces. It is also anticipated that such prophylactic protection against bacteria persists until coating is removed. Anti-bacterial coatings may be prepared from anionic surfactants and anionic polyelectrolytes that serve as monodentate ligands for ions such as $Ag_+$. A method for making an anti-bacterial coating is comprised of: (a) dissolving a silver ion monodentate ligand complex in a suitable solvent to produce a silver ion containing solution, the ligand being any suitable ligand such as, but not limited to, a ligand selected from the group consisting of anionic surfactants and anionic polyelectrolytes; (b) applying the solution to a suitable substrate such as the exterior and/or interior surface of the elastomeric article by dipping and/or spraying; and (c) drying to yield a coating. The terms "anti-bacterial" and "antibacterial" are regarded as equivalent terms.

Lubricant coatings are also applicable, for example, dipping condoms into a lubricant composition and/or by spraying/pumping lubricant onto condoms or by depositing the lubricant by vapor deposition. The lubricant can also be deposited onto the condom as a powder. The lubricant can be water-based (water with a gum thickener), glycol-based (propylene gylcol or butylene glycol or a PEG) or silicone-based (such as a silicone-oil). The lubricant coating may contain additives such as, but not limited to, surfactants, e.g., polyoxyethylene sorbitan monoester.

Preferably, a polyethylene glycol (PEG) based lubricant can be applied onto the articles of manufacture of the present invention. The applied PEG lubricant may be single grade, or multi-graded. It is preferred that for the single grade PEG lubricant to have a molecular weight of in the range 200-1,000 Daltons, whereas mixture of grades of PEG can be used to fine-tune the viscosity, consumer perception, and manufacturability of the elastomeric articles.

The lubricant coating can also be aqueous-based such as a PEG/water mix. In this embodiment the molecular weight of the PEG can be greater than or equal to 10,000 Daltons. Alternatively, the lubricant can be an oil-based lubricant compatible with block copolymers containing ethylene and/or butylene. A preferred embodiment is an elastomeric article such as a condom that is comprised of a block copolymer (i.e. SEBS) and a coating that is comprised of an aqueous polyethylene glycol (PEG).

A fluid lubricant coating may be physically applied, such as by pipette or dosing machine. It may be applied before or after rolling the condom. The lubricant may alternately be a solid bonded to the surface of the condom, with the intent of reducing the coefficient of friction of the condom surface. The lubricant may have been physisorbed or chemisorbed. It may be covalently bonded, such as by the condensation of a silane-containing species to which functional (i.e., surface-friction reducing) moieties may have been added. A solid lubricant may be a continuous film, perhaps selectively applied, or it may be a powder. A lubricant having, for example, a modified ethylene butylene block is applied to the surface of the condom to render the lubricant compatible with the block copolymer.

Alternatively, an insoluble, non-particulate lubricant such as light wax, can be applied to an elastomeric article (i.e. condom) of the present invention. For example, such lubricant can be applied by rolling and packaging the condom, and heating the packaged condom in an oven to a temperature that sufficiently causes the lubricant to spread along the length of the condom. This type of lubricants can also be incorporated into an elastomeric article (i.e. condom) of the present invention, so that the lubricant blooms to the surface of the condom.

Additives of high thermal conductivity can also be used as coatings for the present invention. Non-limiting examples of suitable thermally conductive additives are metal particulates, graphenes, nanocarbon tubes, fullerenes, oxides, or glass beads (silica).

Alternatively, an electrically conductive coating or 3D structure such as a rib can be applied to the elastomeric articles, through covalent bonding or through a mediator compound. Articles with such coatings could be used to direct electricity to drive a device such as a motor. Coatings that are resistant to oil such as natural oils found on human skin, or anti-abrasion coatings are also applicable.

Method of Production

Elastomeric articles can be prepared according to the present invention by dipping a form into an aqueous dispersion and withdrawing the form to yield a film. The water is then evaporated from the film to leave behind a coherent extensible film on the form. More specifically, a condom form is dipped into an aqueous dispersion that comprises water and surfactant, and finely dispersed SEBS, SEPS, SEEBS and/or SEEPS particles in mineral oil. The particles size should be below 2 microns to yield strong and good quality films. The condom can be made from SEBS, SEPS, SEEBS or SEEPS block copolymers, which may be formed of molecules of similar molecular weight or mixtures of two or more molecular weights. To balance the strength and the softness of the dipped article, the PS end blocks should represent about 25 to 35 percent by weight of the total molecule. Non-hydrogenated block co-polymers such SBS or SIS could also be used.

Dipping can also be carried out by means of aqueous dipping with a co-solvent as follows: 1) dispersing the block copolymer in water with the co-solvent; 2) forming the block copolymer hard and soft blocks in the co-solvent; and 3) removing the co-solvent from the block copolymer by a process such as but not limited to applying heat to the material. In the method, the block copolymer and co-solvent are dispersed in water to form the hard and soft blocks of the block copolymer. After the hard and soft blocks are formed, energy such as heat energy is applied to the block copolymer to remove the co-solvent, producing the block copolymer.

In one example, a condom can be made from solution, e.g., by dip forming ("dipping"). Dipping can be achieved by lowering a form such as a condom mandrel into a composition comprising a polymeric material (such as, but not limited to, SEBS) dissolved in solvent, and an amount of plasticizer sufficient for achieving condoms having a modulus of less than about 1.5 MPa, including less than 1.2 MPa and even less than 1.0 MPa at 500% extension, and removing the condom mandrel from the composition to dry (e.g., in an oven at 50° C. for 15 minutes). Alternatively, the formulation can be raised in temperature, forming a molten fluid from which a condom could be cast. Alternatively, injection molding forms the condom. The condom is removed from the mandrels and is then typically dusted with, e.g., dry cornstarch, amorphous silica powder, and etc. The condom has unique tactile and tensile properties (i.e. conformability and low radius of curvature), and modulus below about 1.5 MPa at 500% extension. These properties translate to consumer benefits such as apparent thinness, soft feel and improved tactility over natural rubber latex condoms. This type of condoms does not deform the penis when donned (form fitting), and is less obtrusive during intercourse.

In another embodiment of the present invention, a method is provided for manufacturing a multi-layered elastomeric article, such as but not limited to a condom or a film. Specifically, the method comprises the steps of providing an article composed of first (inner) layer of a polymer through the process of aqueous dipping; dipping the article in a second polymeric material to form the middle layer; and dipping the article in another dispersion of a polymer to form a third (outer) layer. Each layer is formed from SEBS, SEPS, SEEBS, SEEPS-based materials, NRL, PU, SBS, SIS, SB lattices, or mixtures thereof. Copolymers such as SEBS, SEPS, SEEBS, or SEEPS-based materials offer elasticity and softness. Materials such as NRL, PU, SBS, SIS, or SB lattices enhance the tensile strength of the article due to the chemical cross-linking (vulcanization) that occurs at the double bond of the polymers, once the article is cured by the application of heat. Preferably, the outer and inner layers are selected from SEBS, SEPS, SEEBS, SEEPS-based materials, and the inner layer is selected from NRL, PU, SBS, SIS, or SB lattices.

Alternatively, the multi-layer polymer article is comprised of two layers, or at least four layers with each layer that is selected from SEBS, SEPS, SEEBS, SEEPS-based materials, NRL, PU, SBS, SIS, or SB lattices.

In a further embodiment according to the invention is the use of photo curing to increase tensile strength of the articles. In one example, a polymeric material such as an SBC is blended with an initiator substance for photo curing (or in the alternative electron-beam or UV curing), wherein properties of the elastomeric article, such as but not limited to tensile strength, can be controlled by the concentration of the photo-curing initiator substance. Photo curing as used herein substantially avoids the generation of free radicals that can sometimes occur with respect to thermal curing. For example, after the dipping process, an UV and/or e-beam curing is applied for a predetermined time to controllably create cross-links. Cross-linking agents as used herein also include electron-beam irradiation, beta irradiation, gamma irradiation, corona irradiation, silanes, peroxides, allyl compounds and UV radiation with or without cross-linking catalyst.

It must be noted that in the present invention the elastomeric materials, such as condoms having a modulus of less than or about 1.5 MPa at 500% extension, can also be produced without the aid of plasticizers. In this instance the suitable polymeric materials are the same as, but not limited to, those that are listed in "Polymer" section or other suitable polymeric materials that are known in the art.

EXAMPLE 1

SEBS With 186 phr Oil (Parts of Plasticizer Oil Per Hundred Parts of Rubber)

A SEBS-based solvent dipping solution was made by mixing in a 1 gallon glass jar: 741.6 g toluene (obtained from Fisher Scientific), 167.4 g light mineral oil (Callumet Penreco Drakeol™ 7), 90.0 g SEBS (Kraton™ G1654), and 1.00 g mold release agent. The solution was allowed to mix with overhead stirring for 1 hour, and allowed to rest overnight. The following day, a cylindrical dipping vessel was charged with ca. 750 mL of the SEBS solution. A glass condom-shaped mandrel was slowly lowered into the solution, withdrawn at ca. 0.1 in/s, and allowed to dry for ca. 3 minutes with rotation. The dipping procedure was then repeated, forming a condom. The film was allowed to dry in a 55° C. oven for 15 minutes. A security ring was formed by rolling the condom ca. 1" up from the open end. The film was dusted with amorphous silica powder (Cab-o-Sil™ L-90), and carefully removed from the mandrel.

The film was then tested for thickness and tensile properties. The film was approximately 111 microns thick, had a modulus of 0.50 MPa at 500% extension, a tensile strength of 9.46 MPa, and an elongation of 1318% at break.

EXAMPLE 2

SEBS With 112.7 phr Plasticizer Oil

A SEBS-based solvent dipping solution was made by mixing in a 5 gal HDPE vessel: 8.80 kg toluene (obtained from GFS Chemicals), 0.62 kg light mineral oil (Callumet Penreco Drakeol™ 7), 0.44 kg SEBS (Kraton™ G1654), 0.11 kg of SEBS (Kraton™ G1652), and 0.001 kg mold release agent. The solution was allowed to mix with overhead stirring for 1 hour, and allowed to rest overnight. A glass condom-shaped mandrel was slowly lowered into the solution, withdrawn at various rates, and allowed to dry for ca. 3 minutes with rotation. The dipping procedure was then repeated, forming a condom. The film was allowed to dry in a 55° C. oven for 7 minutes. A security ring was formed by rolling the condom ca. 1" up from the open end. The film was dusted with amorphous silica powder (Cab-o-Sil™ L-90), and carefully removed from the mandrel.

Films at various thicknesses were then tested for thickness and tensile properties. A typical film was approximately 66 microns thick, had a modulus of 1.09 MPa at 500% extension, a tensile strength of 14.49 MPa, and an elongation of 1250% at break.

EXAMPLE 3

SEBS With 233.3 phr Plasticizer Oil

A SEBS-based solvent dipping solution was made by mixing in a 1 gallon glass jar: 799 g toluene (obtained from Fisher Scientific), 140 g light mineral oil (Callumet Penreco Drakeol™ 7), 60.0 g SEBS (Kraton™ G1654), and 1.00 g mold release agent. The solution was allowed to mix with overhead stirring for 1 hour, and allowed to rest overnight. The following day, a cylindrical dipping vessel was charged with ca. 750 mL of the SEBS solution. A glass condom-shaped mandrel was slowly lowered into the solution, withdrawn at cal 0.1 in/s, and allowed to dry for ca. 3 minutes with rotation. The dipping procedure was then repeated, forming a condom. The film was allowed to dry in a 55° C. oven for 15 minutes. A security ring was formed by rolling the condom ca. 1" up from the open end. The film was dusted with amorphous silica powder (Cab-o-Sil™ L-90), and carefully removed from the mandrel.

The film was then tested for thickness and tensile properties. The film was approximately 136 microns thick, had a modulus of 0.22 MPa at 500% extension, a tensile strength of 4.72 MPa, and an elongation of 1500% at break.

EXAMPLE 4

SEBS With 100 phr Plasticizer Oil

A solution of SEBS/oil in toluene was prepared in a 3000 mL container by dissolving 51.57 g of SEBS (Kraton G 1651), 77.35 g of SEBS (Kraton G 1650) and 128.92 g of mineral oil USP (Callumet Penreco Drakeol™ 34) in 1350 mL toluene. The solution was agitated for several hours until it was completely dissolved. A surfactant solution was prepared in a 2000 mL container by dissolving 5.4 g of Lankropol K-8300 (from AKZO NOBEL CHEMICALS LTD.), 5.4 g of Sylvaros DRS 214 (from Arizona Chemical) and 775 mL of DI water.

An aqueous dispersion was prepared by slowly adding 155 g of the surfactant water solution into 200 g of the SEBS/oil solution. The dispersion was made via an inverse emulsification process using a IKA lab rotor stator assembly at 20,000 rpm. The dispersion was then concentrated in a rotovap by stripping of the solvent under heat and vacuum.

The aqueous disperson was used to cast films with a draw-down bar on a glass plate. The films were dried at room temperature for about 10-15 minutes, and then placed in oven at 70° C. for 5 minutes. Next, the oven temperature was increased to 120° C. and the films were kept at this temperature for 5-10 minutes. The films were then leached in warm water for 5 minutes. After leaching, the films were dried at 120° C. for 25-30 minutes, cooled at RT, dusted with amorphous silica powder (Cab-o-Sil™ L-90) and stripped off the glass plate.

The films were then tested for thickness and tensile properties. A film of about 270 microns thick, had a modulus of 1.10 MPa at 500% extension, a tensile strength of 8.7 MPa, and an elongation of 950% at break.

EXAMPLE 5

SEEPS With 190.7 phr Plasticizer Oil

A SEEPS-based solvent dipping solution was made by mixing in a 1 gallon glass jar: 737.4 g toluene (obtained from Fisher Scientific), 171.6 g light mineral oil (Callumet Penreco Drakeol™ 7), 90.0 g SEEPS (Kuraray Septon™ 4044), and 1.00 g mold release agent. The solution was allowed to mix with overhead stirring for 1 hour, and allowed to rest overnight. The following day, a cylindrical dipping vessel was charged with ca. 750 mL of the SEEPS solution. A glass condom-shaped mandrel was slowly lowered into the solution, withdrawn at ca. 0.1 in/s, and allowed to dry for ca. 3 minutes with rotation. The dipping procedure was then repeated, forming a condom. The film was allowed to dry in a 55° C. oven for 15 minutes. A security ring was formed by rolling the condom ca. 1" up from the open end. The film was dusted with amorphous silica powder (Cab-o-Sil™ L-90), and carefully removed from the mandrel.

The film was then tested for tensile properties. The film was approximately 89 microns thick, had a modulus of 0.66 MPa at 500% extension, a tensile strength of 11.52 MPa, and an elongation of 1219% at break.

EXAMPLE 6

SEEPS With 150 phr Plasticizer Oil

A solution of SEEPS/oil in toluene was prepared in a 2000 mL container by dissolving 100 g of SEEPS (Kuraray Septon™ 4044) and 150 g of mineral oil USP (Callumet Penreco Drakeol™ 34) in 860 mL toluene (from Fisher Scientific). The solution was agitated for several hours until it was completely dissolved. A surfactant solution was prepared by dissolving 2.5 g of Lankropol K-8300 (from AKZO NOBEL CHEMICALS LTD.) and 2.5 g of Sylvaros DRS 214 (from Arizona Chemical) in 950 mL of DI water.

An aqueous dispersion was prepared by slowly adding 37.5 g of the surfactant water solution into 50 g of the SEEPS/oil solution. The dispersion was made via an inverse emulsification process. The dispersion was then concentrated into a rotovap by stripping of the solvent under heat and vacuum. To prevent coagulation of dispersion in rotovap, hexane (from Fisher Scientific) was used as co-solvent. A SEEPS dispersion with a total solid content of ~38% was thus obtained. The dispersion was used to cast films on a glass plate.

EXAMPLE 7

SEEPS/PIL With Plasticizer

A usable polyisoprene latex ("PIL") was prepared by mixing sodium caseinate stabilizer and an aqueous dispersion of a cure system to IR 401 polyisoprene (Kraton). The cure system comprises ZnO, Sulphur, Zinc Diethyldithiocarbamate ("ZDEC"), diphenylguanidine ("DPG"), and adsorbable organic halogens ("AOx"). The mixing was achieved with a paddle stirrer at 200 rpm. After mixing, the PIL was allowed to mature for 24 hours before use.

An amount of 25 wt. % of the aqueous dispersion of SEEPS (Kuraray Septon™ 4033) was mixed with 75 wt. % of the PIL, and the mixture was stirred at room temperature at 100-150 rpm. A bead of the aqueous SEEPS/PIL dispersion was laid across the top of a 150 mm×100 mm×6 mm glass plate. A K-bar drawn down an even layer film on the glass plaste from the bead. After drawing the film with the K-bar, the plate was dried in air for 5-10 minutes, and the plate was transferred to an oven at 60° C. for 8 minutes to dry the film. The plate was then subsequently heated in an oven at 120° C. for 5 minutes, then cooled in air. To remove the film from the plate, the plate was first soaked in hot water at 50° C. for 5 minutes ("water leaching"), air dried, then heated again in hot water at 40-50° C. for 10 minutes. Afterwards the film was slowly removed from the plate to hang dry. After drying for approximately 3 hours the film was talc dusted on both sides.

The film was tested for tensile properties. The film was approximately 0.04 to 0.06 mm thick, had a modulus of 0.4 MPa at 500% extension, a tensile strength of 0.9 MPa, and an elongation of 734% at break.

EXAMPLE 8

Multi-Layered Elastomeric Product

Four three-layered tubes were made using either SEEPS or SEPS from Kuraray Co., LTD with natural rubber later (NRL) from Revertex™ or polyurethane dispersion (PUD) from Bayer® in the following configurations: SEEPS/NRL/SEEPS, SEEPS/PUD/SEEPS, SEPS/NRL/SEPS, and SEPS/PUD/SEPS.

First, a 20 mm test tube was used as the former. The former was dipped into the first polymeric dispersion of a depth of approximatedly 5 cm by hand, using a continuous in-and-out movement for about five seconds.

Upon removal, the tube was rotated by hand for about 2 minutes in air to dry the dispersion. The tube was then placed in an oven at 90° C. for 5 minutes, then 120° C. for 10 minutes to dry the first film. The tube was cooled for 15 seconds then it was dipped into a second polymeric dispersion of a depth of approximatedly 4 cm, using a continuous in-and-out movement taking about five seconds. The tube was then dried by rotating in air for 1 minute then in oven at 90° C. for 5 minutes.

The tube was removed from the oven and immediately dipped again in a third polymeric dispersion of a depth of approximatedly 2 cm, using a continuous in-and-out moviement taking about five seconds. The tube was rotated in air for 1 minute then in oven at 90° C. for 5 minutes, the 120° C. for 20 minutes to dry the film. Afterwards the multi-layered film was removed from the tube and stored overnight at room temperature before use.

The invention claimed is:

1. An elastomeric article having at least one layer, said at least one layer consisting essentially of 1) at least one styrene-block-ethylene-co-butylene-block-styrene (SEBS) film-forming polymer, and optionally, a polymeric material selected from the group consisting of rubber latex (NRL), synthetic polyisoprene (PI), polyurethane (PU), silicone, styrene-co-butadiene (SB), styrene-co-isoprene (SI), styrene-block-ethylene-co-propylene-block-styrene (SEPS), styrene-block-ethylene-co-ethylene-propylene-block-styrene (SEEPS), and mixtures thereof; 2) at least one plasticizer present in an amount of about 100 to less than 250 parts plasticizer per hundred parts of rubber (phr), and 3) optionally at least one filler selected from calcium carbonate, talc, titanium oxide, silica, clay, carbon black, magnesium carbonate, alumina, and mixtures thereof, wherein said article has a modulus of less than 1.2 MPa at 500% extension, and a thickness of about 66 to no more than 270 microns, wherein said article is a condom.

2. The elastomeric article of claim 1, wherein said article has a modulus of less than 1.0 MPa at 500% extension.

3. The elastomeric article of claim 1, wherein said SEBS is in star form, or a blend of star and linear SEBS.

4. The elastomeric article of claim 1, wherein said plasticizer is selected from mineral oil; dimethicone or its modified form with hydroxyl, carboxylic, cetyl alcohol or amine functionality; vitamin E (tocopherol); straight or slightly branched alkanes; and unsaturated alkanes.

5. The elastomeric article of claim 4, wherein said plasticizer is mineral oil.

6. The elastomeric article of claim 1, wherein said article comprises multiple layers.

7. The elastomeric article of claim 6, wherein at least one said multiple layers is formed from at least one styrene-block-ethylene-co-butylene-block-styrene (SEBS), and optionally, a polymeric material selected from the group consisting of rubber latex (NRL), synthetic polyisoprene (PI), polyurethane (PU), silicone, styrene-co-butadiene (SB), styrene-co-isoprene (SI), styrene-block-ethylene-co-propylene-block-styrene (SEPS), styrene-block-ethylene-co-ethylene-propylene-block-styrene (SEEPS), rubber latex (NRL), synthetic polyisoprene (PI), or water-based polyurethane (PU), and another said layer is formed from rubber latex (NRL), synthetic polyisoprene (PI), or water-based polyurethane (PU).

8. The elastomeric article of claim 1, wherein said article has at least one coating on said at least one layer.

* * * * *